(12) United States Patent
Meijer et al.

(10) Patent No.: US 8,383,834 B2
(45) Date of Patent: Feb. 26, 2013

(54) PROCESS FOR PREPARING UNSATURATED LACTONES

(75) Inventors: John Meijer, Deventer (NL); René Gerritsen, Loosdrecht (NL); Bart Fischer, Leusden (NL)

(73) Assignee: SYMRISE AG, Holzminden (DE)

( * ) Notice: Subject to any disclaimer, the term of this patent is extended or adjusted under 35 U.S.C. 154(b) by 1019 days.

(21) Appl. No.: 11/568,998

(22) PCT Filed: May 10, 2005

(86) PCT No.: PCT/EP2005/052108
§ 371 (c)(1),
(2), (4) Date: Aug. 25, 2009

(87) PCT Pub. No.: WO2005/113533
PCT Pub. Date: Dec. 1, 2005

(65) Prior Publication Data
US 2009/0306411 A1    Dec. 10, 2009

Related U.S. Application Data

(60) Provisional application No. 60/580,732, filed on Jun. 21, 2004.

(30) Foreign Application Priority Data

May 13, 2004 (EP) .................................. 04076417

(51) Int. Cl.
*C07D 313/00* (2006.01)

(52) U.S. Cl. ........................................................ 549/266

(58) Field of Classification Search ................... 549/266
See application file for complete search history.

(56) References Cited

U.S. PATENT DOCUMENTS 5,792,740 A * 8/1998 Mimoun et al. ................. 512/11
6,008,185 A * 12/1999 Bertram et al. ................. 512/12

FOREIGN PATENT DOCUMENTS

| EP | 0424787 | 10/1990 |
| EP | 0862911 | 2/1998 |
| JP | 08-283181 | 10/1996 |
| JP | 10-251684 | 9/1998 |
| JP | 2002-201174 | 7/2002 |

OTHER PUBLICATIONS

Aldrich Catalogue, 1998-1999, p. 148, 714,1537, 4 pages.*
Ogibin, Y.N. et al., Synthesis of nine-, ten-, and fifteen-membered alkenolides by the oxidative cleavage of the bridging C=C bond in 2-oxabicycloalkenes, Russian Chemical Bulletin, International Edition, vol. 50, No. 11, pp. 2149-2155, Nov. 2001.

* cited by examiner

*Primary Examiner* — Taylor Victor Oh
(74) *Attorney, Agent, or Firm* — Roylance, Abrams, Berdo & Goodman, L.L.P.

(57) ABSTRACT

The invention relates to a process for preparing saturated or unsaturated lactones. This process involves reacting a bicyclic compound or a monocyclic compound with hydrogen peroxide in the presence of a first acid having a $pK_a$ of 3 or less and a first organic solvent, thereby forming a hydroperoxide. The obtained mixture comprising the hydroperoxide is subsequently metered to a mixture of a second organic solvent and a dissociation-enhancing catalyst, optionally comprising a second organic acid. The invention also pertains to a process of preparing the hydroperoxide.

15 Claims, No Drawings

PROCESS FOR PREPARING UNSATURATED LACTONES

FIELD OF THE INVENTION

The present invention relates to a process for preparing a lactone according to

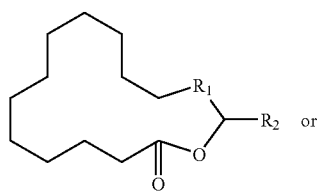

(I)

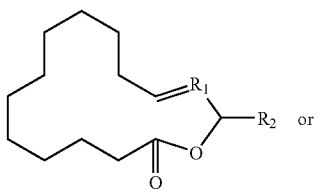

(II)

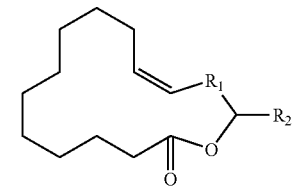

(III)

wherein $R_1$ is a linear or branched hydrocarbon having 1 to 6 carbon atoms and $R_2$ is H or $CH_3$.

BACKGROUND OF THE INVENTION

The invention further relates to a process for preparing the hydroperoxide according to formula

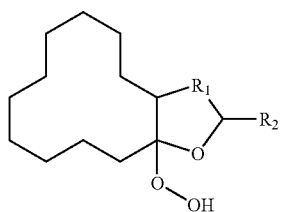

(IV)

wherein $R_1$ is a linear or branched hydrocarbon having 1 to 6 carbon atoms and $R_2$ is H or $CH_3$.

These processes are known from EP 0 424 787. EP 0 424 787 describes that an aqueous solution of sulphuric acid is added to a mixture of 2-(3-hydroxypropyl)-1-cyclododecanone and glacial acetic acid. To this mixture hydrogen peroxide (70%) is added, which reacts with 2-(3-hydroxypropyl)-1-cyclododecanone to form a precipitate of a hydroperoxide of 2-(3-hydroxypropyl)-1-cyclododecanone (referred to as DDP-OOH). The precipitate is subsequently filtered, washed with water and then with diluted $NaHCO_3$, after which it is dried.

The resulting dried precipitate was added in portions to a saturated solution of cupric acetate in methanol. Subsequently, $FeSO_4$ was added to this mixture in two equal portions, after which the resulting mixture underwent various steps to obtain a pure product. The product comprises trans-pentadec-11-en-15-olide, trans-pentadec-12-en-15-olide, cis-pentadec-11-en-15-olide, cis-pentadec-12-en-15-olide, and pentadecanolide.

A disadvantage of this process is that the hydroperoxide must be isolated prior to being reacted with the pentadecenolide, rendering the process complex and expensive. Furthermore, the isolated solid hydroperoxide may be unstable and dangerous.

EP 0 889 945 discloses processes for preparing tetradecenolide and 14-methyl tetradecenolide. Because the process described therein is similar to that described in EP 0 424 787, it has the same disadvantages as described above.

SUMMARY OF THE INVENTION

It is an object of the present invention to provide a process for the preparation of unsaturated lactones as defined in the opening paragraph which is less complex than the processes known in the art.

This object is achieved by a process for preparing a lactone according to formula

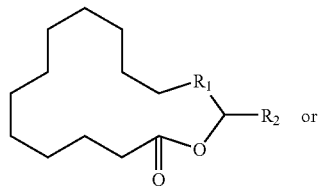

(I)

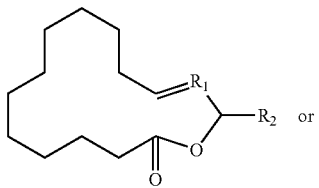

(II)

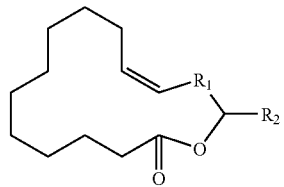

(III)

wherein $R_1$ is a linear or branched hydrocarbon having 1 to 6 carbon atoms and $R_2$ is H or $CH_3$, the process comprising the steps of:

(a) reacting a bicyclic compound according to formula

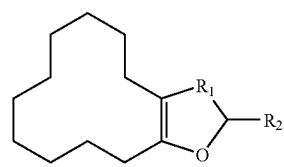

(V)

or a monocyclic compound according to formula

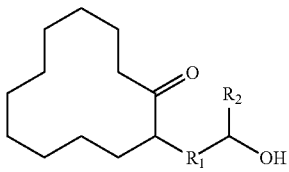

(VI)

wherein $R_1$ and $R_2$ are as defined above, with hydrogen peroxide in the presence of a first acid having a $pK_a$ of 3 or less and a first organic solvent containing less than 5 wt % of water, calculated on the total weight of the first organic solvent, thereby forming a composition comprising a hydroperoxide according to formula

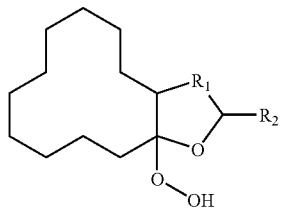

(IV)

wherein $R_1$ and $R_2$ are as defined above; and
(b) metering the composition comprising the hydroperoxide to a mixture of a second organic solvent and a dissociation-enhancing catalyst.

The process of the present invention does not need a step to isolate the hydroperoxide, i.e. filtering, washing, and drying of the hydroperoxide, after step (a) is performed, rendering the process much simpler than those of the state of the art which do prescribe such an isolation step. The composition comprising the hydroperoxide resulting from step (a) can be metered directly to a mixture of a second organic solvent and a dissociation-enhancing catalyst. The said isolation step brings about aqueous waste streams which may require further processing to clean them. Consequently, hydroperoxide isolation is time consuming and expensive and moreover is not desirable from an environmental point of view. Isolation of the pure hydroperoxide may further cause hazardous and dangerous situations. As the process of the invention does not require the isolation step, this process is much simpler, safer, and faster than the known processes for the production of saturated and unsaturated lactones.

DETAILED DESCRIPTION OF THE INVENTION

In the context of the present application the term "the total weight of the reaction mixture of step (a)" refers to the total weight of the compounds used in step (a) before the reaction of step (a) takes place, including the bicyclic compound as defined above, the hydrogen peroxide, the first acid, and the first organic solvent.

The desired product of the process of the invention determines the choice of the starting compound, i.e. the bicyclic or monocyclic compound as defined above. Examples of bicyclic compounds are 13-oxabicyclo[10.3.0]pentadec-1(12)-ene, 14-methyl-13-oxabicyclo[10.3.0]pentadec-1(12)-ene, 13-oxabicyclo[10.4.0]hexadec-1(12)-ene (DDP), 14-methyl-13-oxabicyclo[10.4.0]hexadec-1(12)-ene, 13-oxa-bicyclo[10.5.0]heptadec-1(12)-ene, 14-methyl-13-oxabicyclo[10.5.0]heptadec-1(12)-ene, 13-oxabicyclo[10.6.0]octadec-1(12)-ene, and 14-methyl-13-oxabicyclo-[10.6.0]octadec-1(12)-ene.

Examples of monocyclic compounds are 2-(2-hydroxyethyl)-1-cyclododecanone, 2-(2-hydroxypropyl)-1-cyclododecanone, 2-(3-hydroxypropyl)-1-cyclododecanone, 2-(3-hydroxybutyl)-1-cyclododecanone, 2-(4-hydroxybutyl)-1-cyclododecanone, 2-(4-hydroxypentyl)-1-cyclododecanone, 2-(5-hydroxypentyl)-1-cyclododecanone, and 2-(5-hydroxyhexyl)-1-cyclododecanone.

The amount of bicyclic or monocyclic compound in the reaction mixture is at least 1 wt %, preferably at least 2 wt %, and most preferably at least 5 wt %, and at most 60 wt %, preferably at most 55 wt %, and most preferably at most 50 wt %, calculated on the total weight of the reaction mixture of step (a).

The hydrogen peroxide usually is an aqueous solution of the hydrogen peroxide, e.g. a concentrated 70 wt % aqueous hydrogen peroxide solution.

The amount of hydrogen peroxide solution which is initially added to the reaction mixture is at least 1 wt %, preferably at least 2 wt %, and most preferably at least 3 wt %, and at most 20 wt %, preferably at most 15 wt %, and most preferably at most 12 wt %, calculated on the total weight of the reaction mixture of step (a).

The first acid having a $pK_a$ of 3 or less may be an inorganic or an organic acid. Examples of inorganic acids are sulphuric acid, hydrochloric acid, nitric acid, and phosphoric acid. Examples of organic acids are monochloroacetic acid, alkylbenzene sulphonic acid, wherein the alkyl group is a linear or branched $C_2$-$C_{16}$ alkyl, and alkyl sulphonic acid, wherein the alkyl group is a linear or branched $C_2$-$C_{16}$ alkyl. Preferably, the first acid is alkylbenzene sulphonic acid, wherein the alkyl group is a linear or branched $C_2$-$C_{16}$ alkyl, an alkyl sulphonic acid, wherein the alkyl group is a linear or branched $C_2$-$C_{16}$ alkyl, or a mixture thereof. More preferably, the first acid is an alkylbenzene sulphonic acid, wherein the alkyl group is a linear or branched $C_{10}$-$C_{13}$ alkyl, an alkyl sulphonic acid, wherein the alkyl group is a linear or branched $C_2$-$C_{16}$ alkyl, or a mixture thereof. The first acid is most preferably a $C_{10}$ alkylbenzene sulphonic acid, a $C_{10}$ alkyl sulphonic acid, or a mixture thereof.

The required $pK_a$ value of 3 or less of the first acid is preferred for step (a) of the process of the invention. If the $pK_a$ value is above 3, the reaction to the hydroperoxide will proceed slowly, which renders the process economically unattractive.

Preferably, the first acid is chosen such that it dissolves in the hydrogen peroxide, so that adding them simultaneously is relatively easy and leads to an improved reaction efficiency.

Additionally, it is preferred that the first acid used dissolves in the first organic solvent, so that the first acid will easily migrate into the first solvent and become available for the reactants present in the first organic solvent. This will lead to a higher reaction efficiency and a higher space time yield.

If the first acid is a $C_2$-$C_{16}$ alkylbenzene sulphonic acid, a $C_2$-$C_{16}$ alkyl sulphonic acid, or a mixture thereof, the first acid generally serves as a catalyst, i.e. it facilitates the reaction in step (a) of the process of the invention while being consumed not at all or only to a small extent. As a consequence, only small amounts can be added as compared to conventional processes. The first acid is generally added in an amount of at least 0.001 wt %, preferably at least 0.005 wt %, and most preferably at least 0.01 wt %, calculated on the total weight of the reaction mixture of step (a), and at most 2 wt %, preferably at most 1.5 wt %, and most preferably at most 1 wt %, calculated on the total weight of the reaction mixture of step (a).

The first organic solvent suitable for use in step (a) of the process of the invention may be an organic solvent which is inert under the reaction conditions of step (a). Preferably, the first organic solvent contains less than 5 wt %, preferably less than 2 wt % of water, calculated on the total weight of the first organic solvent.

Examples of such solvents are acetates, e.g. methyl tert-amyl acetate, butyl acetate, 2-metylpropyl acetate, etc., ketones such as 4-methyl-2-pentanone, 5-methyl-2-hexanone, etc., formates, propionates, alcohols such as methanol, ethanol, propanol, 1-butanol, etc., aliphatic hydrocarbons, both cyclic and acyclic, e.g. hexane, octane, decane, cyclohexane, Isopar® (ex Exxon), Shellsol® (ex Shell), etc., and aromatic hydrocarbons, e.g. benzene, toluene, o-xylene, m-xylene, p-xylene, etc. Preferred first organic solvents are the aromatic hydrocarbons. The most preferred solvents are benzene, toluene, o-xylene, m-xylene, p-xylene. In these solvents the bicyclic compound or monocyclic compound as defined above is well dissolved, enabling a higher reaction rate and a smaller amount of the first acid compared to conventional processes (where a large amount of sulphuric acid is used, see e.g. EP 0 424 787). Furthermore, the amount of $H_2O_2$ used in step (a) can be reduced. In addition, the hydroperoxide resulting from the reaction of step (a) is also well dispersed in these preferred organic solvents, which is advantageous when the resulting composition is metered to the mixture of step (b) because of better stability and good pourability of the slurry comprising the hydroperoxide crystallites.

The amount of first organic solvent generally is at least 20 wt %, preferably at least 25 wt %, and most preferably at least 30 wt %, calculated on the total weight of the reaction mixture of step (a), and at most 90 wt %, preferably at most 80 wt %, and most preferably at most 70 wt %, calculated on the total weight of the reaction mixture of step (a).

Step (a) of the process of the present invention can be carried out in various ways known to the man skilled in the art. In a first way, the bicyclic or monocyclic compound is added to the first organic solvent first. The first acid and the hydrogen peroxide will subsequently be added to the mixture of bicyclic or monocyclic compound and first organic solvent. Preferably, the first acid is dissolved in the hydrogen peroxide before addition to the bicyclic/monocyclic compound-solvent mixture. The advantage is that in this way a better reaction efficiency and a higher yield are obtained and that a smaller amount of hydrogen peroxide may be necessary.

The first acid and the hydrogen peroxide may be added simultaneously or one after the other. If these compounds are added one after the other, it is preferred to add the first acid first and then the hydrogen peroxide. Each of the first acid and the hydrogen peroxide may be added in one go or in portions of the same or different size. They may also be continuously metered during a period of time.

Alternatively, the first acid and the hydrogen peroxide are added to the first organic solvent. To this mixture the bicyclic or monoculclic compound is added in one go or in portions of the same or different size. The bicyclic or monoculclic compound may also be continuously metered during a period of time.

The temperature at which the reaction of step (a) takes place is not essential and may be between −10 and 80° C., preferably between 0 and 70° C., most preferably between 10 and 60° C. At a temperature below −10° C. the reaction of step (a) proceeds slowly. If the reaction is carried out at a temperature above 80° C., the selectivity towards the desired hydroperoxide will diminish.

The composition comprising the hydroperoxide obtained after reaction of the bicyclic or monocyclic compound with the hydrogen peroxide according to step (a) is subsequently metered to a mixture of a second organic solvent and a dissociation-enhancing catalyst. In the context of the present application the term "the total weight of the reaction mixture of step (b)" refers to the total weight of the compounds used in step (b) before the reaction of step (b) takes place, including the composition obtained from step (a) and metered in step (b), the second organic solvent, and the dissociation-enhancing catalyst.

The second organic solvent may be an organic solvent which is inert under the reaction conditions of step (b). Preferably, the second organic solvent is essentially free of water. "Essentially free of water" means that prior to the dissociation of the hydroperoxide the solvent contains less than 5 wt %, preferably less than 2 wt % of water, calculated on the total weight of the second organic solvent.

Examples of such solvents are acetates, e.g. methyl tert-amyl acetate, butyl acetate, 2-methylpropyl acetate, etc., ketones such as 4-methyl-2-pentanone, 5-methyl-2-hexanone, etc., formates, propionates, alcohols such as methanol, ethanol, propanol, 1-butanol etc., aliphatic hydrocarbons, both cyclic and acyclic, e.g. hexane, octane, decane, cyclohexane, etc., and aromatic hydrocarbons, e.g. benzene, toluene, o-xylene, m-xylene, p-xylene, etc. Preferred second organic solvents are the aromatic hydrocarbons. The most preferred solvents are benzene, toluene, o-xylene, m-xylene, p-xylene. These solvents are particularly advantageous, as water can be easily removed from the azeotrope of this solvent and water already present or produced in step (b) of the process of the invention.

Preferably, the first and second organic solvents are the same. This enables good mixing of the composition resulting from step (a) into the mixture of the second organic solvent and the dissociation-enhancing catalyst, rendering a good dissociation rate.

A further advantage is that the solvent can be easily recycled and used in either one of steps (a) and (b) of the process of the invention.

The amount of the second organic solvent generally is at least 2 wt %, preferably at least 5 wt %, and most preferably at least 10 wt %, calculated on the total weight of the reaction mixture of step (b), and at most 95 wt %, preferably at most 80 wt %, and most preferably at most 70 wt %, calculated on the total weight of the reaction mixture of step (b).

The dissociation-enhancing catalyst preferably comprises a salt or complex of a metal ion, with the metal ion being selected from the group consisting of copper, iron, cobalt, and manganese. Preferably, the metal ion is a metal ion of copper. Examples of a salt of a metal ion is a sulphite, bisulphate, sulphate, phosphate, nitrite, nitrate, or halide, e.g. chloride, iodide, and bromide. Examples of metal ion complexes comprise an organic group selected from the group consisting of acetate, acetylacetonate, propionate, butyrate, stearate, caproate, ethylcaproate, pivalate, valerate, isovalerate, laurate, 2-ethylhexanoate, octanoate, decanoate, and naphthenate.

The amount of the dissociation-enhancing catalyst generally is at least 0.001 wt %, preferably at least 0.005 wt %, and most preferably at least 0.01 wt %, calculated on the total weight of the reaction mixture of step (b), and at most 15 wt %, preferably at most 10 wt %, and most preferably at most 5 wt %, calculated on the total weight of the reaction mixture of step (b).

Optionally, a second organic acid may be added in step (a) at any time before, during or after the reaction, or in step (b). Addition of the second organic acid in step (b) is less desirable because the hydroperoxide may be hydrolysed to a considerable extent. It is preferred to add the second organic acid to the composition comprising the hydroperoxide before this composition is metered according to step (b) of the process of the invention. The second organic acid is selected from a group consisting of acetic acid, acetyl acetonic acid, propionic acid, butyric acid, stearic acid, caproic acid, ethylcaproic acid, pivalic acid, valeric acid, isovaleric acid, lauric acid, 2-ethylhexanoic acid, octanoic acid, decanoic acid, naphthenic acid. Preferably, the second organic acid is the same as the acid from which the organic group of the dissociation-enhancing catalyst originates. In this way, the number of contaminants in the product of step (b) is minimised, rendering a separation step, if necessary, easier.

The second organic acid aids in the dissociation of the hydroperoxide, rendering an improved yield of the unsaturated lactone.

The second organic acid is generally added in an amount of at least 0.001 wt %, preferably at least 0.005 wt %, and most preferably at least 0.01 wt %, calculated on the total weight of the reaction mixture of step (a), and at most 10 wt %, preferably at most 8 wt %, and most preferably at most 5 wt %, calculated on the total weight of the reaction mixture of step (a).

Without wishing to be bound by any theory, Applicant believes that the acid value of the reaction mixture influences the final composition of the product. The acid value of the reaction mixture is determined using methods known to the man skilled in the art. An example of such a method is potentiometric titration. The acid value of the reaction mixture is preferably less than 10 mg KOH/g reaction mixture. Above an acid value of 10 mg KOH/g reaction mixture, the selectivity towards desired saturated or unsaturated lactone decreases due to hydrolysation, which is undesirable. A higher selectivity towards the unsaturated lactone is generally obtained when the acid value of the reaction mixture is between 2 and 10 mg KOH/g reaction mixture.

Step (b) of the process of the present invention can be carried out in various ways known to the man skilled in the art. Generally, the dissociation-enhancing catalyst will be added to the second organic solvent first. The composition comprising the hydroperoxide obtained from step (a) may be metered in one go or in portions of the same or different size. The composition may also be continuously metered during a desired period of time at the same or a varying metering rate.

In step (b) of the process of the invention, water is formed during the dissociation of the hydroperoxide, rendering an azeotrope of water and the first and second organic solvents. The temperature used in step (b) is preferably chosen so that water is continuously distilled while the dissociation of the hydroperoxide proceeds. Distillation processes are known to the man skilled in the art, e.g. atmospheric distillation and distillation at pressures below atmospheric pressure. In this way, the amount of water is kept at a minimum during dissociation, which is desirable to minimise the amount of by-products that are formed through hydrolysis.

Generally, the dissociation of step (b) takes place at elevated temperature. The temperature of the reaction mixture typically is between 40° C. and the boiling temperature of the reaction mixture formed. Preferably, the temperature of the reaction mixture is the boiling temperature of the reaction mixture.

The lactones of the invention may be saturated or unsaturated. Examples of saturated lactones are 14-methyl-14-tetradecanolide, 15-methyl-15-penta-decanolide, 14-methyl-15-pentadecanolide, 15-hexadecanolide, 17-heptadecanolide, 16-methyl-16-hexadecanolide, 15-methyl-16-hexadecanolide, 17-methyl-16-heptadecanolide, and 16-methyl-17-heptadecanolide.

Examples of unsaturated lactones obtained using the process of the invention are cis-15-pentadec-11-enolide, trans-15-pentadec-11-enolide, cis-15-pentadec-12-enolide, trans-15-pentadec-12-enolide, cis-14-methyl-15-pentadec-11-enolide, trans-14-methyl-15-pentadec-11-enolide, cis-15-methyl-15-pentadec-11-enolide, trans-15-methyl-15-pentadec-11-enolide, cis-14-methyl-15-pentadec-12-enolide, trans-14-methyl-15-pentadec-12-enolide, cis-15-methyl-15-pentadec-12-enolide, trans-15-methyl-15-pentadec-12-enolide, cis-16-hexadec-11-olide, trans-16-hexa-dec-11-olide, cis-16-hexadec-12-olide, trans-16-hexadec-12-olide, cis-15-methyl-16-hexadec-11-olide, trans-15-methyl-16-hexadec-11-olide, cis-16-methyl-16-hexadec-11-olide, trans-16-methyl-16-hexadec-11-olide, cis-15-methyl-16-hexa-dec-12-olide, trans-15-methyl-16-hexadec-12-olide, cis-16-methyl-16-hexadec-12-olide, trans-16-methyl-16-hexadec-12-olide, cis-17-heptadec-11-enolide, trans-17-heptadec-11-enolide, cis-17-heptadec-12-enolide, trans-17-heptadec-12-enolide, cis-16-methyl-17-heptadec-11-enolide, trans-16-methyl-17-heptadec-11-enolide, cis-17-methyl-17-heptadec-11-enolide, trans-17-methyl-17-heptadec-11-enolide, cis-16-methyl-17-heptadec-12-enolide, trans-16-methyl-17-heptadec-12-enolide, cis-17-methyl-17-heptadec-12-enolide, trans-17-methyl-17-heptadec-12-enolide.

As is indicated above, the unsaturated lactones can be prepared in the cis- and/or the trans-configuration, i.e. the double bond present in the lactone is in the cis- or trans-configuration.

The ratio between saturated and unsaturated lactones in the final product can be influenced and depends on various process parameters, such as the type and amount of dissociation-enhancing catalyst used, the reaction temperature, the type of first and/or second solvent, for instance.

The unsaturated lactones obtained using the process of the invention can be hydrogenated to form the corresponding saturated lactone. Such hydrogenation processes are known in the art. An example of such a process can be found in EP 1 243 587. The thus obtained saturated lactones are suitable for use as fragrances in perfumes, substances used for cleaning, for example.

The invention further relates to a process for preparing the hydroperoxide according to formula

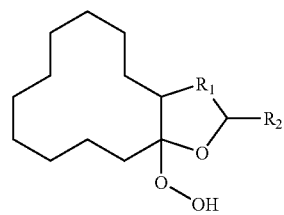

(IV)

wherein $R_1$ is a linear or branched hydrocarbon having 1 to 6 carbon atoms and $R_2$ is H or $CH_3$, the process comprising the steps of
(a) reacting a bicyclic compound according to formula

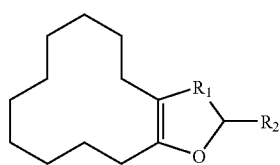

(V)

or a monocyclic compound according to formula

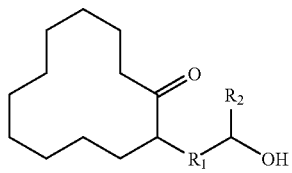

(VI)

wherein $R_1$ and $R_2$ are as defined above, with hydrogen peroxide in the presence of a first acid having a $pK_a$ of 3 or less and a first organic solvent containing less than 5 wt % of water, calculated on the total weight of the first organic solvent. The first acid and the first organic solvent are defined above.

The invention is illustrated in the following Examples.

EXAMPLE

Step (a)

To a 1-liter reactor 223 g 13-oxabicyclo[10.4.0]hexadec-1(12)-ene (DDP), 351 g toluene, and 7.8 g 2-ethylhexanoic acid are added and mixed for 10 minutes. 0.2 g linear $C_{10}$ alkyl benzene sulphonic acid is dissolved in 40 ml of an aqueous 70% hydrogen peroxide solution. The resulting hydrogen peroxide solution is metered to the 1-liter reactor over a period of 10 minutes while the temperature is not allowed to exceed 30° C. The obtained reaction mixture is stirred for one hour. A composition containing the hydroperoxide of 2-(3-hydroxypropyl)-1-cyclododecanone (DDP-OOH) and toluene is obtained.

Step (b)

3 g Cu(II) stearate are dissolved in 132 g toluene. The Cu(II) stearate/toluene mixture is heated to a temperature of about 100° C. Subsequently, the composition obtained in step (a) is metered to the heated Cu(II) stearate/toluene mixture during a period of 50 minutes, after which the resulting mixture is stirred for 30 minutes. During the metering and the subsequent stirring of the reaction mixture, the reaction mixture was continuously distilled at the boiling temperature of the water/toluene azeotrope. A mixture of cis-pentadec-11-en-15-olide, trans-pentadec-11-en-15-olide, cis-pentadec-12-en-15-olide, and trans-pentadec-12-en-15-olide in toluene is obtained. 87% by weight of the DDP initially present in step (a) was converted to pentadecanolide and pentadecenolide.

After toluene removal the final product mixture contained:
DDP (starting material): 1.2% (in GC area %)
Pentadecanolide: 1.7%
Trans-pentadecenolide: 61.9%
Cis-pentadecenolide: 22.8%

These values are presented in GC area % and were determined using a gas chromatograph according to the method described in EP 0 424 787.

It is noted that the amount of DDP in the final product is low compared to the amount observed in conventional processes.

The invention claimed is:
1. A process for preparing a lactone according to formula I, II, or III:

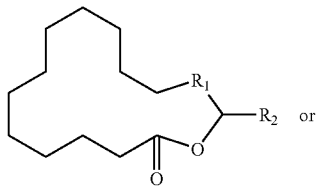

(I)

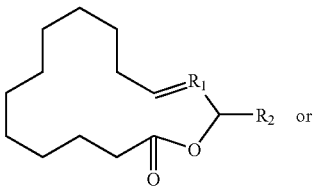

(II)

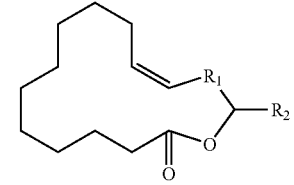

(III)

wherein $R_1$ is a linear or branched hydrocarbon having 1 to 6 carbon atoms and $R_2$ is H or $CH_3$, the process comprising the steps of:
(a) reacting a bicyclic compound according to formula (V)

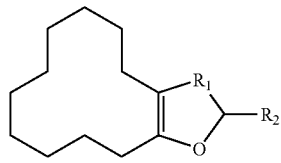

(V)

or a monocyclic compound according to formula (VI)

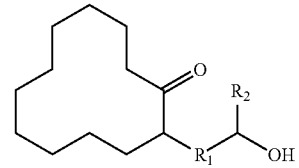

(VI)

wherein $R_1$ and $R_2$ are as defined above, with hydrogen peroxide in the presence of a first acid having a $pK_a$ of 3 or less and a first organic solvent containing less than 5 wt % of water, calculated on the total weight of the first organic solvent, under conditions sufficient to form an intermediate composition comprising a hydroperoxide according to formula (IV)

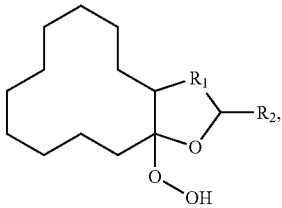

(IV)

wherein $R_1$ and $R_2$ are as defined above; and (b) metering the intermediate composition comprising the hydroperoxide to a mixture of a second organic solvent and a catalytic amount of a dissociation-enhancing catalyst under conditions sufficient to form said lactone, where said dissociation-enhancing catalyst comprises a salt or complex of a metal ion selected from the group consisting of copper, iron, cobalt, and manganese, and said intermediate composition is the reaction product of step (a) without isolating said hydroperoxide of formula (IV).

2. Process according to claim 1 wherein the first acid is selected form a group consisting of alkyl benzene sulphonic acids, wherein the alkyl group is a linear or branched $C_2$-$C_{16}$ alkyl, alkyl sulphonic acids, wherein the alkyl group is a linear or branched $C_2$-$C_{16}$ alkyl, and mixtures thereof.

3. Process according to claim 1 wherein the first organic solvent is selected from the group consisting of benzene, toluene, p-xylene, m-xylene, o-xylene, and mixtures thereof.

4. Process according to claim 1 wherein the first and second organic solvents are the same.

5. Process according to claim 1 wherein the salt is selected from a group consisting of sulphite, bisulphate, sulphate, nitrite, nitrate, phosphate, chloride, bromide or iodide, or the complex comprises an organic group selected from the group consisting of acetate, acetylacetonate, propionate, butyrate, stearate, caproate, ethylcaproate, pivalate, valerate, isovalerate, laurate, 2-ethylhexanoate, octanoate, decanoate, and naphthenate.

6. Process according to claim 1 wherein a second organic acid is added in step (a).

7. Process according to claim 6 wherein the second organic acid is selected from a group consisting of acetic acid, acetylacetonic acid, propionic acid, butyric acid, stearic acid, caproic acid, ethylcaproic acid, pivalic acid, valeric acid, isovaleric acid, lauric acid, 2-ethylhexanoic acid, octanoic acid, decanoic acid, naphthenic acid.

8. Process according to claim 6 wherein the second organic acid is the same as the acid from which the organic group originates.

9. Process according to claim 6 wherein the trans-configuration of the lactone is predominantly formed.

10. A process for preparing a hydroperoxide according to formula (IV)

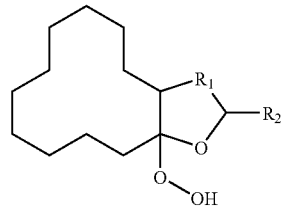

(IV)

wherein $R_1$ is a linear or branched hydrocarbon having 1 to 6 carbon atoms and $R_2$ is H or $CH_3$, the process comprising the steps of (a) reacting a monocyclic compound according to formula (VI)

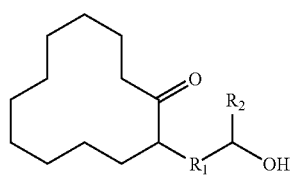

(VI)

wherein $R_1$ and $R_2$ are as defined above, with hydrogen peroxide in the presence of a first acid having a $pK_a$ of 3 or less and a first organic solvent containing less than 5 wt % of water, calculated on the total weight of the first organic solvent.

11. Process according to claim 1 wherein said intermediate composition is metered directly from said step (a) to said step (b) without isolating the hydroperoxide from the intermediate composition.

12. Process according to claim 1 wherein the first acid is selected form a group consisting of alkyl benzene sulphonic acids, wherein the alkyl group is a linear or branched $C_2$-$C_{16}$ alkyl, alkyl sulphonic acids, wherein the alkyl group is a linear or branched $C_2$-$C_{16}$ alkyl, and mixtures thereof.

13. Process according to claim 1 wherein the first organic solvent is selected from the group consisting of benzene, toluene, p-xylene, m-xylene, o-xylene, and mixtures thereof.

14. A process for preparing a lactone according to formula I, II, or III:

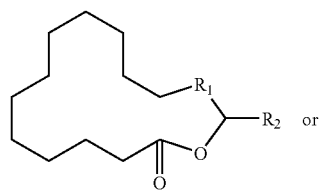

(I)

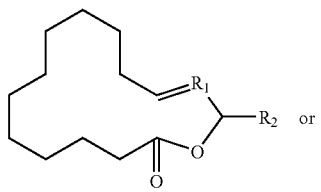

(II)

-continued

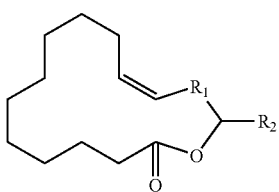
(III)

wherein R₁ is a linear or branched hydrocarbon having 1 to 6 carbon atoms and R₂ is H or CH₃, the process comprising the steps of:
(a) reacting a monocyclic compound according to formula (VI)

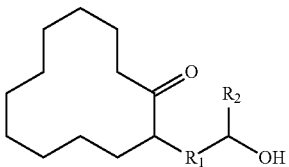
(VI)

wherein R₁ and R₂ are as defined above, with hydrogen peroxide in the presence of a first acid having a pK$_a$ of 3 or less and a first organic solvent containing less than 5 wt % of water, calculated on the total weight of the first organic solvent, under conditions sufficient to form a reaction mixture containing a hydroperoxide according to formula (IV)

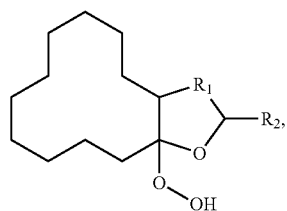
(IV)

wherein R₁ and R₂ are as defined above; and
(b) metering the reaction mixture containing the hydroperoxide to a mixture of a second organic solvent to form said lactone.

15. The process of claim 14, wherein said lactone is formed in the presence of a dissociation-enhancing catalyst comprising a salt or complex of metal ion selected from the group consisting of copper, iron, cobalt and manganese.

* * * * *